United States Patent
Savage

(10) Patent No.: US 6,530,899 B1
(45) Date of Patent: Mar. 11, 2003

(54) CATHETER HAVING A SPEAR SHAPED TIP

(75) Inventor: James Savage, San Marcos, CA (US)

(73) Assignee: Jomed Inc., Rancho Cordova, CA (US)

( * ) Notice: Subject to any disclaimer, the term of this patent is extended or adjusted under 35 U.S.C. 154(b) by 0 days.

(21) Appl. No.: 09/536,433

(22) Filed: Mar. 27, 2000

(51) Int. Cl.[7] .............................................. A61M 29/00
(52) U.S. Cl. ............................ 604/103.04; 604/102.02; 604/528; 604/164.13
(58) Field of Search .................... 604/164.13, 103.04, 604/102.02, 264, 528, 523; 600/585

(56) References Cited

U.S. PATENT DOCUMENTS

| | | | |
|---|---|---|---|
| 2,751,911 A | | 6/1956 | Held |
| 4,362,150 A | * | 12/1982 | Lombardi et al. ............. 600/18 |
| 4,646,719 A | * | 3/1987 | Neuman et al. ............... 600/18 |
| 4,976,703 A | | 12/1990 | Franetzki et al. |
| 5,217,435 A | * | 6/1993 | Kring .......................... 600/585 |
| 5,339,833 A | * | 8/1994 | Berthiaume et al. ......... 600/585 |
| 5,356,388 A | | 10/1994 | Sepetka et al. |
| 5,383,853 A | * | 1/1995 | Jung et al. .............. 604/103.04 |
| 5,500,012 A | * | 3/1996 | Brucker et al. ................ 604/22 |
| 5,591,129 A | * | 1/1997 | Shoup et al. ............. 604/103.1 |
| 5,695,507 A | * | 12/1997 | Auth et al. ..................... 604/22 |
| 5,700,252 A | | 12/1997 | Klingenstein |
| 5,810,867 A | * | 9/1998 | Zarbatany et al. ........ 604/96.01 |
| 5,921,971 A | * | 7/1999 | Agro et al. .................. 604/264 |
| 6,059,713 A | * | 5/2000 | Urick et al. .................... 600/3 |
| 6,152,909 A | * | 11/2000 | Bagaoisan et al. .......... 604/173 |
| 6,190,358 B1 | * | 2/2001 | Fitzmaurice et al. ... 604/102.02 |
| 6,290,693 B1 | * | 9/2001 | Jung et al. ................... 600/585 |

OTHER PUBLICATIONS

International Search Report in corresponding PCT Application No. PCT/US01/08909, dated Jul. 20, 2001 and received Jul. 23, 2001.

* cited by examiner

*Primary Examiner*—Brian L. Casler
*Assistant Examiner*—Jeremy Thissell
(74) *Attorney, Agent, or Firm*—Leydig, Voit & Mayer, Ltd.

(57) ABSTRACT

A catheter (200) includes a spear shaped tip (130). In one embodiment, the spear shaped tip (130) is part of a spear shaped tip assembly (100) that includes a swivel assembly. The swivel assembly provides for improved trackability of the catheter (200) over a guide wire. The spear shaped tip catheter of the present invention can be designed in numerous configurations including over-the-wire and rapid exchange versions.

12 Claims, 2 Drawing Sheets

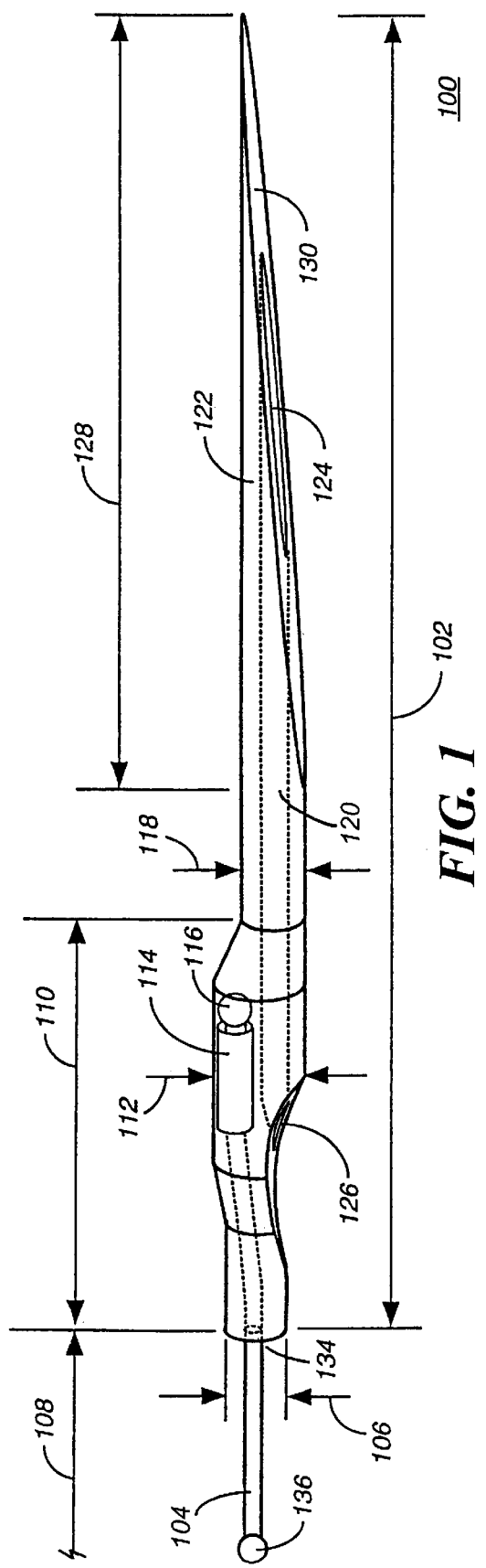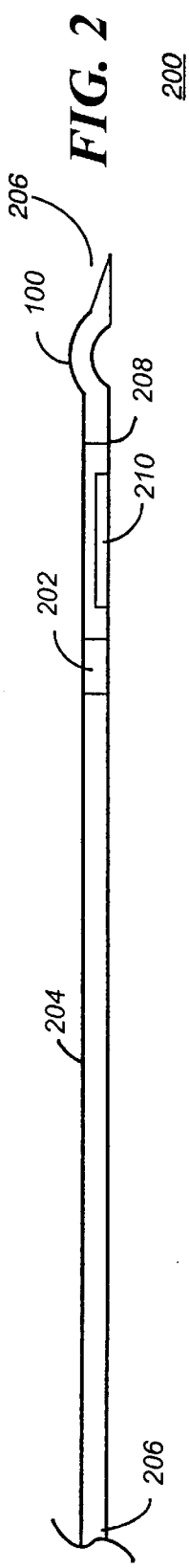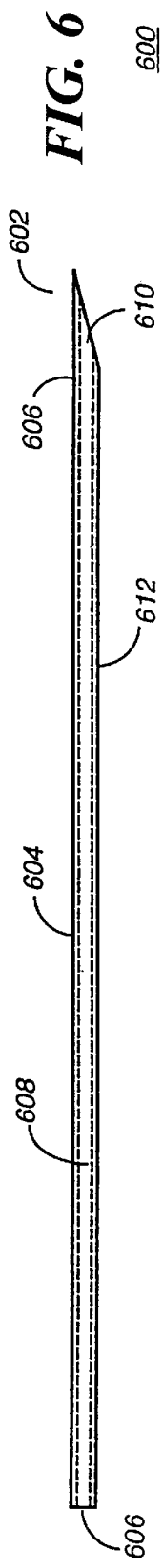

CATHETER HAVING A SPEAR SHAPED TIP

FIELD OF THE INVENTION

This invention relates in general to the field of medical devices, more particularly, this invention relates to a medical catheter having a substantially spear shaped tip.

BACKGROUND OF THE INVENTION

Catheters are well known in the medical field. The typical procedure for inserting a catheter into a patient is to first feed a guide wire into the patient until the distal end of the guide wire has reached a target location inside the patient, for example, a portion of a blood vessel that has a stenosis. Once the guide wire is in place, a catheter is feed through the proximal end of the guide wire. The catheter is then feed into the patient and tracked along the guide wire until the catheter has also reached the target location.

There are two main ways by which catheters track over a guide wire, the first is an "over-the-wire" design in which the guide wire lumen extends from approximately the far distal tip of the catheter to the far proximal end. The second is a monorail also referred to as a rapid-exchange system where the guide wire lumen is shorter (typically much shorter) than the length of the catheter.

Most catheters in use today use a tapered tip in order to follow a guide wire through an artery. Due to the relative bluntness of the tip, even the very best formed tips may have trouble crossing obstacles such as stents, occlusions or tight turns located in the artery. This presents a problem in medical procedures were as one example, a stenosis may have developed in an artery where a stent placed in a previous procedure needs to be crossed in order to get to the stenosis. A need thus exists in the art for a catheter, which can minimize the above-mentioned problem.

BRIEF DESCRIPTION OF THE DRAWINGS

FIG. 1 shows a spear shaped catheter tip in accordance with one embodiment of the invention.

FIG. 2 shows a catheter having the catheter tip shown in FIG. 1.

FIG. 6 shows an alternate embodiment of a catheter having an integral spear shaped tip in accordance with the invention.

DETAILED DESCRIPTION OF THE PREFERRED EMBODIMENT

Figure 3:
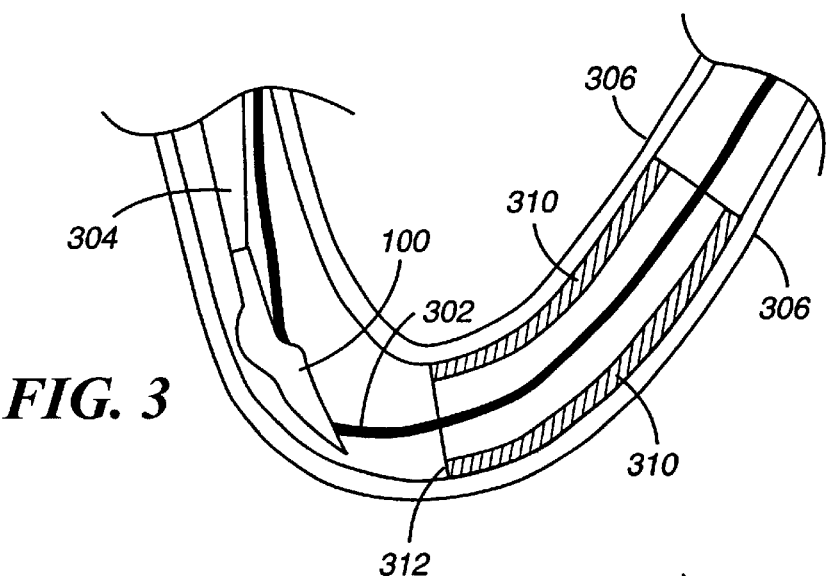
FIGS. 3–5 illustrates the catheter in FIG. 2 crossing a stent in accordance with the invention.

Referring now to the drawings and in particular to FIG. 1 there is shown a spear shaped catheter tip assembly 100 including a spear shaped catheter tip housing 122 in accordance with the preferred embodiment. In this embodiment, the spear shaped catheter tip housing 122 is coupled to the catheter body (not shown) using a swivel tip assembly. The spear shaped catheter tip housing 122 is preferably formed from high-density polyethylene ("HDPE"). Although HDPE is used in the preferred embodiment, the spear shaped catheter tip housing 122 can be formed of other well-known materials used for medical applications as is known in the art.

The distal end of the catheter tip housing 122 has an angled section that will be referred to as a substantially spear shaped tip 130 given its resemblance to a spear. The housing 122 further includes a guide wire passageway or lumen 120. The guide wire passageway 120 has proximal 126 and distal 124 apertures or openings. The guide wire passageway 120 is used for receiving a guide wire (not shown). Once the guide wire is inserted into passageway 120 a catheter (shown in FIG. 2 as one example) having the spear shaped tip 100 is tracked along the guide wire until it reaches the target location within a vessel.

Given that the guide wire passageway 120 does not extend the length of the catheter and actually only extends for a portion of the spear shaped tip-housing 100, this design is considered a monorail design. The spear shaped tip-housing 122 is attached to the distal end of a catheter shaft 204 as shown in FIG. 2 via a swivel tip assembly. The swivel tip assembly that includes a bushing 114, wire 104 and spherical member 116, which is just the distal end of wire 104 formed into a spherical member.

The use of the swivel tip assembly helps reduce the snagging or grabbing of the guide wire by the catheter as since the spear shaped tip housing 122 is able to rotate about the guide wire and helps maintain a loose coupling to the guide wire. This is especially helpful in reducing snagging of the guide wire while the catheter is being maneuvered through one or more tight turns along a vessel. The ability of the spear shaped tip housing 110 to freely swivel or rotate about wire 102 helps reduce any binding forces formed between the catheter and the guide wire as the catheter tracks along the guide wire.

In the preferred embodiment, spear shaped tip housing 122 has an overall length 102 of approximately 15 millimeters (0.59-inch). Guide wire passageway or lumen 120 has a diameter of approximately 0.432 mm (0.017-inch) and the distal portion of housing 122 has an outside diameter 118, at the noted location, of approximately 0.57 mm (0.0225-inch). The outside diameter of housing 122 at its proximal end 106 is approximately 0.61 mm (0.024 inch). There is a slight bulge in swivel tip housing 122 at 112 where the outside diameter is approximately 0.86 mm (0.034 inch). The distal end 128 of the housing 122 is approximately 8 mm (0.31 inch) in length. This distal end 128 is where the housing is formed into a spear shaped form. Proximal end 110 has a length of approximately 5 mm (0.20 inch).

The proximal guide wire opening 126 of the housing is angled (also referred to as a "skive") to further reduce the possibility of the guide wire that gets inserted through the guide wire lumen 120 from hanging up with the housing 122, as housing 122 is navigated through tight turns.

Attached to the spear shaped tip housing 122 as shown in FIG. 1 is an attachment member 104 that is inserted into housing 122 via aperture 134. In the preferred embodiment attachment member 104 comprises a piece of wire. Wire 102 is made from 304 stainless steel, although other materials known in the art can be substituted therefor. Wire 104 attaches the housing 122 to a flexible elongate member such as a catheter (not shown). In the preferred embodiment, the swivel wire has an extension length 108 of approximately 3 mm (0.120 inch). The proximal end of the wire 136, which is preferably formed into a substantially spherical shape, can be attached to a catheter using an adhesive, heat bonding, or any one of a number of other conventional attachment techniques. Preferably the attachment of the wire 104 to the catheter is done at the distal end of the catheter, although in different designs the attachment point may vary.

Instead of using a stainless steel wire as the attachment member 104, other materials suitable for insertion into humans or animals and which would provide for a strong enough attachment so that the housing 122 does not break away from the catheter may be used. Stainless steel wire is the preferred material in this embodiment, given the way the swivel tip assembly is formed by heat-flowing the plastic in a jacket or mold.

At the distal end of the swivel wire 104 is a substantially spherical member such as a ball or sphere 116. A bushing 114 which is attached to the housing 122 prevents the wire 104 from detaching given that sphere 116 has a larger diameter than the diameter of the bushing's opening. Heating the end of swivel wire 104 in a fixture forms the ball tip 116 (as well as proximal sphere 136). Any burrs that may form from this process are removed prior to insertion of the swivel wire 104 into spear tip shaped housing 122.

Alternatively, instead of making the ball 116 integral to swivel wire 104, ball tip 116 can be formed from a separate spherical member that is attached to swivel wire 104 by use of a number of known attachment techniques (e.g., welding, soldering, crimping, etc.). Instead of using a spherical member 116 as shown, any other shaped member (e.g., a cone shaped member, etc.) that would prevent the detachment of the attachment wire 104 from the rest of the swivel assembly, and that would allow for the free rotation of the housing 122 about the attachment member or wire 104, can be used.

In close proximity to ball tip 116 is a bushing 114, which is slid into swivel wire 104 from the opposite end of swivel wire 104 until it reaches ball tip 116. Once the ball tip 116 and bushing 114 are inserted and pushed into to the end of aperture 134 which provides for a slip fit for ball tip 116 and bushing 114, the spear tip shaped housing 122 is heated using a hot torch fixture or other heat source. This heating causes the polyethylene housing to melt around the ball tip 116 and bushing 114 and fuses the bushing 114 and captures it within the housing 122.

Once housing 122 is cooled, the swivel wire 104 is rotated (using the portion external to housing 122) causing ball tip 116 and swivel wire 104 to break free of any melted polyethylene which may have adhered to them. Bushing 114 which is firmly attached to housing 122 by the heating process prevents the detachment of swivel wire 104 from housing 122. Ball 116 and bushing 114 form a swivel or rotation point, which allows for housing 122 to swivel about, wire 104. Although a ball and bushing have been utilized in the preferred embodiment, other designs which allow housing 122 to swivel or rotate about attachment joint designs may be used (e.g., a bearing encased in a housing member, etc.).

Swivel wire 104 in the preferred embodiment has a diameter of approximately 0.15 mm+/–0.05 mm(0.006-inch+/–0.0002 inch). The ball tip 116 has a diameter of approximately 0.28 mm+/–0.025 mm (0.011-inch+/–0.001 inch). Bushing 114 has a length of approximately 1.52 mm (0.060 inch), an outside aperture diameter 304 of 0.33 mm+/–(0.013+/–0.00135 inch) and an inside aperture diameter of 0.178 mm+/–0.0127 mm (0.007+/–0.0005-inch).

A more detailed discussion of the manufacturing of the swivel tip assembly can be found in a U.S. patent application entitled "A swivel Tip Assembly and Catheter using Same", by Jung et al., having Ser. No. 09/354,992, and assigned to the same assignee of this application. This U.S. patent application is hereby incorporated by reference as if fully set forth herein. The spear shaped tip 130 can be preferably manufactured with the use of a spear cut shaped mandrel having an outer diameter that allows its insertion into the distal guide wire lumen of a catheter shaft. First, the mandrel is placed inside the distal tip of the catheter shaft, with the spear cut on the mandrel located distally. Then, from the proximal to the distal end of the catheter shaft, a cutting device such as a razor blade, is followed along the spear cut shape of the mandrel. Finally, the mandrel is removed, and the spear shaped tip is formed. Although the above embodiment has shown the swivel assembly, for example in FIG. 1 comprising bushing 114 and sphere 116 located within the sphere tipped housing 122, the swivel joint could be placed in the catheter shaft 204 (see FIG. 2) in an alternate embodiment.

In FIG. 2, there is shown a flexible elongate member assembly such as a spear shaped tipped catheter 200 in accordance with the invention. Catheter 200 includes the spear shaped catheter tip assembly 100 discussed above. The housing assembly 100 is attached to the distal end 208 of catheter shaft 204. Catheter assembly 200 may a include a treatment section 210 which can include among other things a balloon for performing balloon angioplasty, a radiation source, or other treatment devices. The catheter 200 may further include an intravascular ultrasound transducer assembly 202 such as those manufactured by EndoSonics Corporation of Rancho Cordova, Calif.

The proximal end 136 of the swivel wire 104 is attached to the distal end 208 of the catheter 200 by bonding the wire using a medical grade adhesive. Other known attachment techniques such as welding or crimping the swivel wire 104 to the distal end 208 of catheter 200 can also be used depending on the particular design. The proximal end 206 of catheter 200 can be attached to a catheter connector (not shown) as is well known in the art. The catheter connector can include a guide wire lumen port, an inflation port in the case catheter 200 includes an angioplasty balloon, a radiation source lumen port for introducing radioactive sources, etc.

Figure 4:
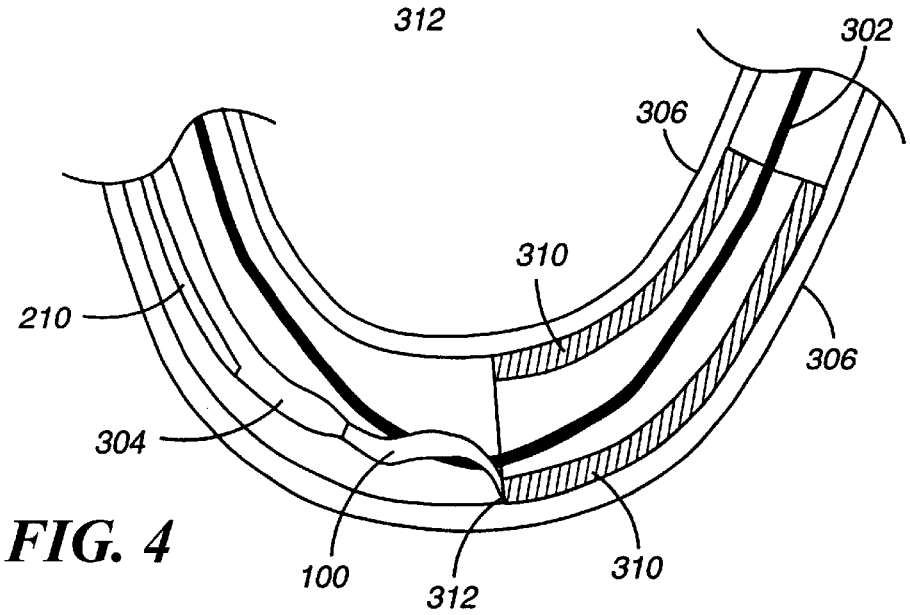
Figure 5:
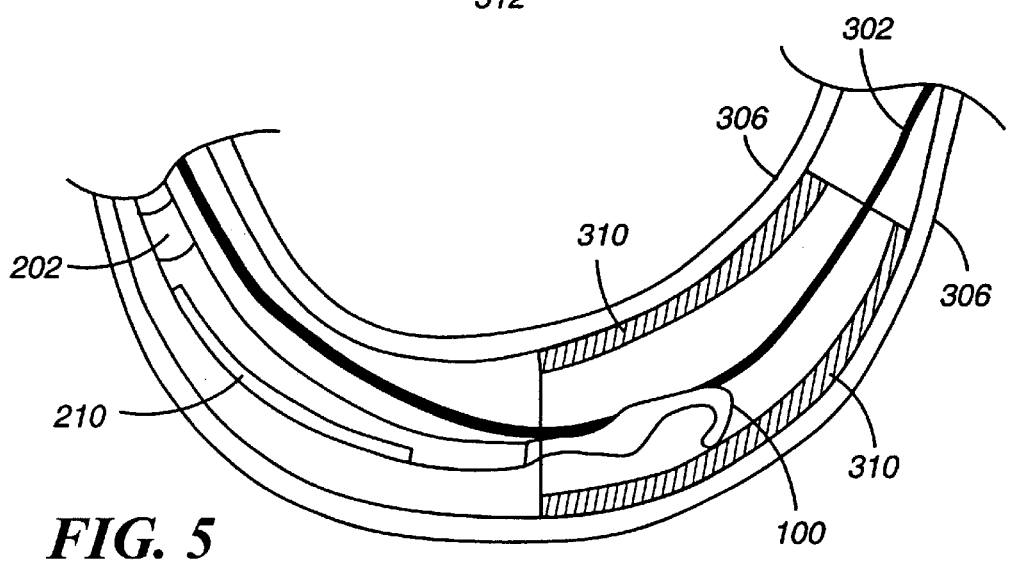

Referring now to FIGS. 3–5 there is shown how the substantially spear shaped tipped catheter housing 100 attached to a catheter shaft 304 helps to cross through an obstruction, such as a stent 310, located in an artery 306. As shown in FIG. 3, the spear tipped shaped housing 100 is tracked along a guide wire 302. When the spear shaped tip housing 100 reaches stent wall edge 312 it flexes, and immediately bends since the spear shaped tip is so flexible, this causes the catheter to be pushed upward as shown in FIG. 4. With the catheter pushed upwards, the catheter is now able to easily cross through the stent as shown in FIG. 5. There is almost no feel of hitting against an obstacle, in this particular case stent 310, which compares favorably against other prior art catheters. The spear shaped tip 130 of the present invention provides for improved "pushability" and "trackability" of catheters using the spear shaped tip 130.

The spear tipped housing 100 provides for an improvement over other catheters in that the spear shaped tip with its added flexibility minimizes the catheter getting stuck while crossing vessel obstructions, such as stents, hardened occlusions, etc. The addition of having the spear shaped housing 100 attached using a swivel assembly as shown in FIG. 1 helps prevent the grabbing of the guide wire 302 as the catheter assembly 200 is tracked over the guide wire 302. The swivel or rotation action provided by the swivel tip assembly helps reduce snagging of the guide wire 302 especially while the catheter assembly 200 is being tracked over a tight bend in a vessel (e.g., artery).

Although the above embodiment, has shown the spear tipped housing 122 attached to the catheter shaft 204 via the swivel assembly discussed in FIG. 1, the spear shaped catheter tip of the present invention can be used in a catheter having no swivel attachment. In FIG. 6, there is shown a catheter 600 having a substantially spear shaped tip 602 which is formed integrally to the catheter shaft 604, or alternatively, is formed separately of the catheter shaft 604 and fixed to the distal end 606 of the catheter shaft. If the substantially spear shaped tip 602 is formed as a separate member, it can be attached to the catheter shaft using any one of a number of well known mechanical attachment techniques, such as medical grade epoxy, ultrasonic welding, mechanical force fit, etc.

Catheter 600 includes a guide wire lumen 604 that in this case is of an over-the-wire configuration given that it runs substantially along the entire length of the catheter. The guide wire lumen 604 has a proximal opening 606 and a distal opening 610. Alternatively, if the proximal opening where located around location 612, it would be considered a monorail or rapid-exchange configuration.

The added flexibility and pointed design of the substantially spear shaped tip of the present invention allows for catheters to cross over stents and other vessel obstruction with reduced effort. This helps improve the "trackability" of the catheter over a guide wire, and helps reduce the time it takes a physician to place the catheter in the right location. This of course helps reduce the time a physician takes to perform a procedure.

While the invention has been described in conjunction with specific embodiments, it is evident that many alternatives, modifications, permutations and variations will become apparent to those skilled in the art in light of the foregoing description. For example, increasing the angle or length of the cut, which forms the spear shape, can modify the spear shape tip 130 shown in FIG. 1. Also, the type of material used for the spear shaped tip can be selected depending on the design at hand to provide for different levels of flexibility. Furthermore, as previously explained the spear shaped tip can be part of a swivel assembly, be integral or fixed to the distal end of a catheter, and can used with rapid exchange, or over-the-wire guide wire lumen designs.

What is claimed is:

1. An intravascular catheter, comprising:
   a catheter shaft having proximal and distal ends;
   a substantially spear shaped tip located at the distal end of the catheter shaft;
   a guide wire lumen extending through the catheter shaft and a portion of the spear shaped tip such that an opening terminates before a distal end of the spear shaped tip; and
   wherein the spear shaped tip is angled at a portion distal of the opening such that the portion distal of the opening bends substantially and deflects backwards when it encounters an obstruction within a vessel.

2. A catheter as defined in claim 1, wherein the spear shaped tip is integral to the catheter shaft.

3. A catheter as defined in claim 1, wherein the substantially spear shaped tip is part of a separate housing that is attached to the catheter shaft.

4. A catheter as defined in claim 3, wherein the separate housing having the substantially spear shaped tip is attached to the distal end of the catheter shaft.

5. A catheter as defined in claim 3, wherein the separate housing having the substantially spear shaped tip includes a swivel joint located within the housing, and the housing is attached to the catheter shaft using an attachment member having one end attached to the swivel joint and the other end attached to the catheter shaft.

6. A catheter as defined in claim 5, wherein the attachment member comprises a wire and the swivel joint allows the housing to rotate freely about the wire.

7. A catheter as defined in claim 1, wherein the guide wire lumen comprises an over-the-wire configuration and extends to a proximal opening disposed at the proximal end of the catheter shaft.

8. A catheter as defined in claim 1, further including a guide wire lumen in a rapid-exchange configuration, wherein the guide wire lumen has a distal opening located at the spear shaped tip and a proximal opening located distally of the proximal end of the catheter shaft.

9. A catheter tip assembly which can track along a guide wire, comprising:
   a housing having a substantially spear shaped tip;
   a guide wire lumen located within the housing member such that an opening terminates before a distal end of the spear shaped tip; and
   wherein the spear shaped tip is angled at a portion distal of the opening such that the portion distal of the opening bends substantially and deflects backwards when it encounters an obstruction within a vessel.

10. A catheter tip assembly as defined in claim 9, further including a swivel joint assembly attached to the housing member.

11. A catheter tip assembly as defined in claim 9, wherein the guide wire lumen proximally terminates at a proximal opening.

12. A catheter tip assembly as defined in claim 11, wherein the proximal opening is skived.

* * * * *